US011020608B2

(12) United States Patent
Lopath

(10) Patent No.: US 11,020,608 B2
(45) Date of Patent: *Jun. 1, 2021

(54) CORNEAL MEASUREMENT AND CONTROL OF CORNEAL CROSSLINKING

(71) Applicant: TECLens, LLC, St. James, NY (US)

(72) Inventor: Patrick David Lopath, Stamford, CT (US)

(73) Assignee: TECLens, LLC, St. James, NY (US)

( * ) Notice: Subject to any disclaimer, the term of this patent is extended or adjusted under 35 U.S.C. 154(b) by 706 days.

This patent is subject to a terminal disclaimer.

(21) Appl. No.: 15/445,351

(22) Filed: Feb. 28, 2017

(65) Prior Publication Data

US 2017/0246471 A1    Aug. 31, 2017

Related U.S. Application Data

(60) Provisional application No. 62/301,040, filed on Feb. 29, 2016.

(51) Int. Cl.
*A61F 9/007* (2006.01)
*A61B 3/10* (2006.01)
(Continued)

(52) U.S. Cl.
CPC ............ *A61N 5/062* (2013.01); *A61B 3/1005* (2013.01); *A61B 8/10* (2013.01); *A61B 8/485* (2013.01);
(Continued)

(58) Field of Classification Search
CPC ........ A61B 3/1005; A61B 8/10; A61N 5/062; A61N 2005/063; A61N 2005/0648; A61N 2005/0626; A61F 9/008
See application file for complete search history.

(56) References Cited

U.S. PATENT DOCUMENTS 5,861,955 A * 1/1999 Gordon .................. A61B 3/107
356/511
9,883,970 B2 * 2/2018 Lopath ..................... A61F 9/008
(Continued)

FOREIGN PATENT DOCUMENTS

CN     103153396 A     6/2013
CN     103565401 A     2/2014
(Continued)

OTHER PUBLICATIONS

Moramarco A. et. al., "Corneal stromal demarcation line after accelerated crosslinking using continuous and pulsed light", Journal Cataract and Refractive Surgery, vol. 41, No. 11, Nov. 2015, pp. 2546-2551.
(Continued)

*Primary Examiner* — Allen Porter
*Assistant Examiner* — Adreanne A. Arnold
(74) *Attorney, Agent, or Firm* — Lerner, David, Littenberg, Krumholz & Mentlik, LLP

(57) ABSTRACT

Systems and methods for monitoring properties of the cornea and controlling the crosslinking treatment. The thickness of the cornea during crosslinking may be measured by using ultrasonic reflections to determine an anterior distance ($D_1'$) between a reference location (37) on a device resting on the eye and an anterior surface (66) of the cornea and to determine a posterior distance ($D_3'$) between a posterior surface (63) of the cornea and an element of the eye such as an anterior surface (72) of the lens of the eye. These distances are subtracted from a reference distance ($D_0$) between the reference location and the element of the eye. The reference distance ($D_0$) may be determined using ultrasonic reflections to determine the corresponding anterior and posterior distances and the thickness ($D_2$) of the cornea prior to crosslinking. The speed of sound in the cornea during
(Continued)

crosslinking may be derived using the thickness (D2') and time of flight of ultrasound through the cornea. The position of the cornea relative to a reference location may be determined. In still other embodiments, location of a surface of demarcation (86) within the cornea formed as a result of crosslinking may be determined. Still other embodiments provide for determination of one or more resonant frequencies of the cornea, and for measurement of responses of the cornea to applied forces, such as displacement and rebound velocity. The properties of the cornea may be used as proxies for the extent of crosslinking, and a light source (48, 348) used to induce crosslinking may be controlled in response to such proxies.

13 Claims, 5 Drawing Sheets

(51) Int. Cl.
   *A61N 5/06* (2006.01)
   *A61F 9/008* (2006.01)
   *A61B 8/08* (2006.01)
   *A61B 8/10* (2006.01)
   *A61F 9/00* (2006.01)

(52) U.S. Cl.
   CPC ............ *A61F 9/008* (2013.01); *A61F 9/0017* (2013.01); *A61F 9/0079* (2013.01); *A61B 8/0858* (2013.01); *A61F 2009/00872* (2013.01); *A61N 2005/063* (2013.01); *A61N 2005/0626* (2013.01); *A61N 2005/0648* (2013.01)

(56) References Cited

U.S. PATENT DOCUMENTS

| | | |
|---|---|---|
| 2004/0193054 A1* | 9/2004 | Leblanc .................. A61B 3/16 600/452 |
| 2006/0032507 A1 | 2/2006 | Tu |
| 2006/0173314 A1* | 8/2006 | Leblanc .................. A61B 3/16 600/437 |
| 2006/0184214 A1 | 8/2006 | McDaniel |
| 2013/0085370 A1 | 4/2013 | Friedman et al. |
| 2013/0211389 A1 | 8/2013 | Chuck et al. |
| 2014/0379054 A1 | 12/2014 | Cooper et al. |

FOREIGN PATENT DOCUMENTS

| | | |
|---|---|---|
| WO | 2009124271 A1 | 10/2009 |
| WO | 2015200817 A1 | 12/2015 |

OTHER PUBLICATIONS

Acka et al., Observation of sound-induced corneal vibrational modes by optical coherence tomography, Biomedical Optics Express vol. 6, No. 9 (2015), pp. 3313-3319.
U.S. Appl. No. 61/839,016, filed Jun. 25, 2013.
U.S. Appl. No. 62/095,416, filed Dec. 22, 2014.
Extended European Search Report with Written Opinion for Application No. 20161058.0 dated Jun. 26, 2020, 10 pages.
Chinese Search Report for Application No. 201780026307.0 dated Oct. 22, 2020, 3 pages.

\* cited by examiner

CORNEAL MEASUREMENT AND CONTROL OF CORNEAL CROSSLINKING

CROSS-REFERENCE TO RELATED APPLICATIONS

The present application claims the benefit of the filing date of U.S. Provisional Patent Application No. 62/301,040, filed Feb. 29, 2016, the disclosure of which is hereby incorporated herein by reference.

BACKGROUND OF THE INVENTION

The present invention relates to methods and apparatus for measuring certain properties of the cornea, and for control of corneal crosslinking ("CXL").

The vision of a human or other mammalian subject can be modified by crosslinking substances within the cornea of the eye. A photoactivated crosslinking agent such as riboflavin is applied to the cornea. Light at a wavelength selected to activate the crosslinking facilitator is applied. Where the crosslinking facilitator is riboflavin, the light typically is ultraviolet or blue light. The activated agent causes crosslinking of substances within the cornea. The crosslinking changes the mechanical properties of the cornea. For example, the crosslinking stiffens the cornea. These changes can result in stabilization of pathological conditions, such as keratoconus, or in alterations to the shape of the cornea. This technique can be used to correct defects in vision such as myopia, hyperopia, or astigmatism. For myopia (nearsightedness), the center of the cornea is stiffened; for hyperopia (farsightedness), an annulus around the periphery of the cornea is stiffened. For more complicated corrections such as astigmatism, custom patterns are used.

In some applications, the light is applied as a beam directed into the eye from a device remote from the eye. In other applications, the light is applied by a device that rests on the eye. As disclosed in U.S. Patent Application Publication No. 2014/0379054 ("the '054 Publication") and U.S. Provisional Patent Application No. 61/839,016 ("the '016 Provisional"), the disclosures of which are hereby incorporated by reference herein, light can be applied to the eye through a structure having a form, size, and shape resembling that of a contact lens such as a scleral contact lens. The structure may incorporate an optically dispersive element, i.e., a light scattering element. Light may be directed into the dispersive element and scattered so that the scattered light passes into the eye from the dispersive element. This arrangement has numerous advantages. For example, the patient may be able to close his or her eye during the treatment, so that the structure is disposed between the eyelid and the eye.

CXL changes the mechanical properties of the cornea by creating chemical bonds in the corneal stroma. These bonds (crosslinks) increase the stiffness of the cornea in the region crosslinked. This increased stiffness changes the balance between the corneal tension and the intraocular pressure. Through mechanisms not completely understand in the field, physiologic processes reshape the cornea. The full extent of this reshaping develops over days to weeks after the CXL treatment. Therefore, the full extent of reshaping that will be caused by CXL treatment cannot be measured during the treatment. The amount of reshaping, and thus the degree of vision correction, is determined by a number of treatment parameters, including the amount and rate of energy delivery, the treatment time and the aperture of the treated area on the cornea. The amount of reshaping also may be influenced by factors such as the oxygen saturation of the cornea during irradiation; the amount of crosslinking agent present in the cornea during irradiation and physiological differences between patients.

As with any therapeutic energy delivery modality, it is desirable to control the irradiation of the eye so as to deliver a dose of radiation that will yield the desired procedural outcome, such as a desired degree of reshaping. Because numerous factors control the relationship between the light energy applied to the cornea during irradiation and the amount of reshaping achieved, it is difficult to achieve a precise degree of reshaping by selecting a dose of energy in advance, based on a priori knowledge of a relationship between dose and reshaping, and then simply applying the selected dose.

Accordingly, further improvement would be desirable.

SUMMARY OF THE INVENTION

The present invention provides methods and apparatus for measuring certain properties and responses of the cornea, and for conducting and controlling corneal crosslinking using such properties and responses.

DETAILED DESCRIPTION

Figure 1:
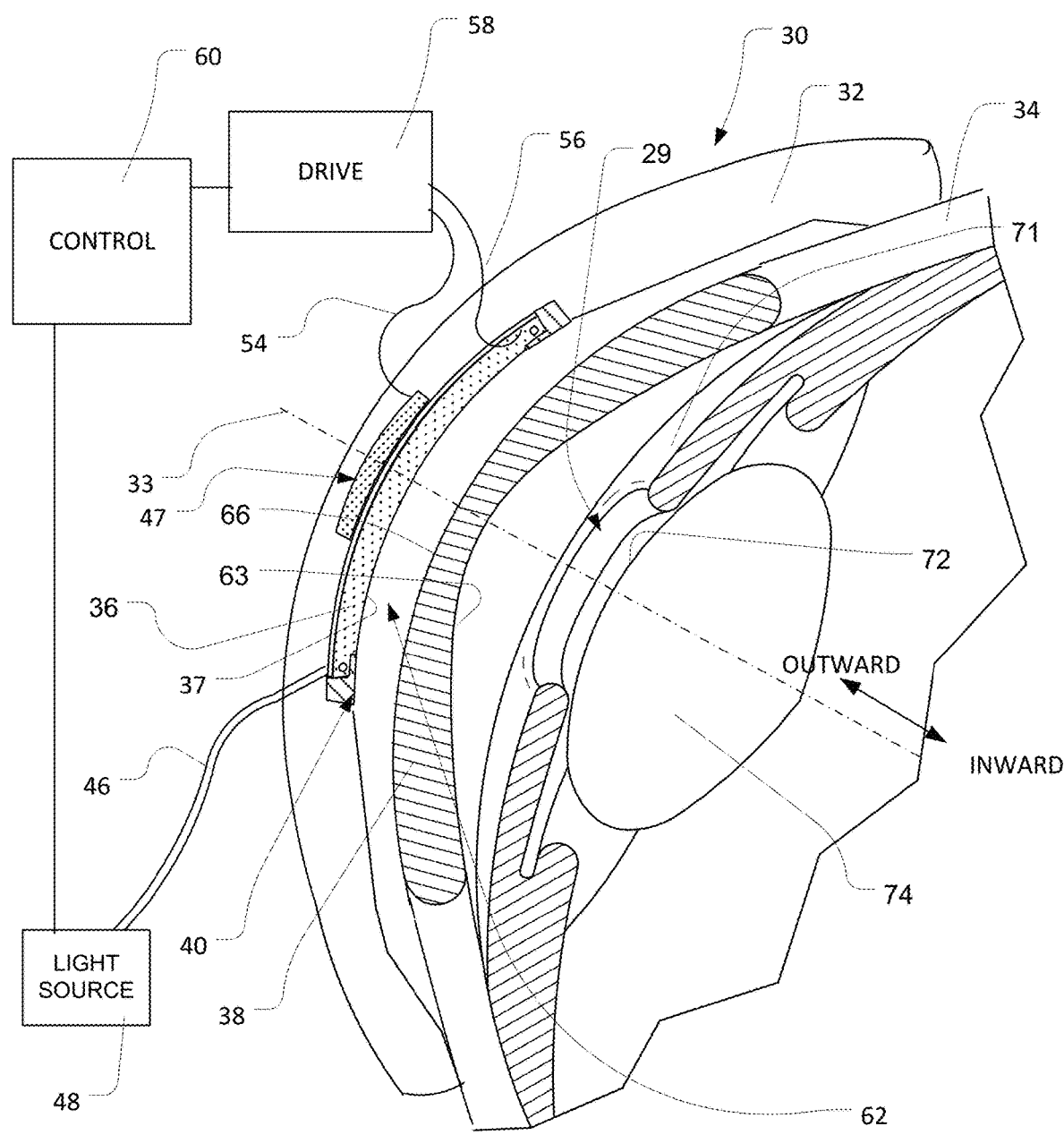
FIG. 1 is a partially sectional, partially block diagrammatic view depicting apparatus in accordance with one embodiment of the present invention in conjunction with an eye of a subject.
Figure 2:
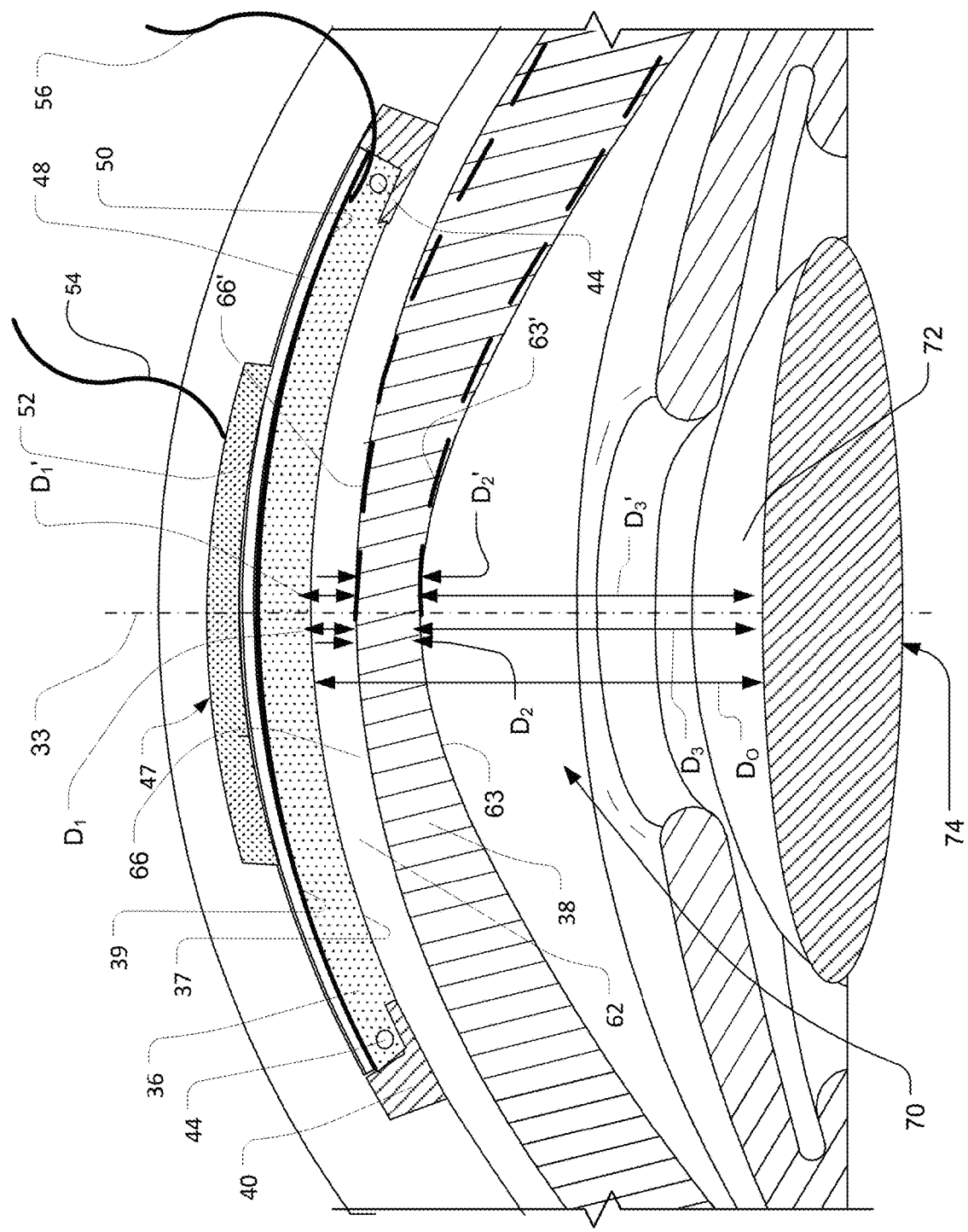
FIG. 2 is a diagrammatic sectional view depicting an eye of a subject during two stages of a method according to one embodiment of the invention.

A system according to one embodiment of the invention includes a device 30 having a structure adapted to overlie and rest upon the anterior surface of the eye. The structure of the device includes a housing 32 generally in the form and size of a scleral contact lens having a central axis 33. The housing includes a peripheral portion adapted to bear on the sclera 34 of the eye when the device is in place on the eye as depicted in FIG. 1. When the device is in place on the eye, the central axis 33 of the housing is aligned with the pupil 29 of the eye and with the center of the cornea 38 of the eye. The axis 33 extends inwardly toward the eye and outwardly away from the eye. The structure further includes a diffuser 36 disposed in a central portion of housing. As described in greater detail in the '054 Publication, the diffuser is formed from a material that is arranged to scatter ultraviolet light as the light passes through it, and thus disperse the light passing through the material. Such a material is referred to herein as an optically scattering material or optically dispersive material. For example, the material may be as a clear silicone polymer with particles such as barium sulfate dispersed in the polymer. The diffuser may be in the form of a layer or dome having an inner surface 37 facing toward the eye when the structure is in place. The device further includes a fiber carrier 40 defining an aperture aligned with a portion of the diffuser 36. In the particular embodiment depicted, the aperture is in the form of a circular opening as, for example, about 6 mm in diameter, although other sizes and shapes may be employed. As best seen in FIG. 2, one or more optical fibers 44 extend within the fiber carrier 40 and are in optical communication with the diffuser 36. The optical fibers 44 are connected in optical communication with a light source such as a laser 48. The foregoing features of the device may be as disclosed in the '054 Publication, and may also include the features disclosed in U.S. Provisional Patent Application No. 62/095,416, filed Dec. 22, 2014 ("the '416 Provisional"), the disclosure of which is hereby incorporated by reference herein.

The device further includes one or more ultrasonic transducers 47. In the embodiment depicted, transducer 47 incorporates a layer of a piezoelectric material, preferably a polymeric piezoelectric material such as polyvinylidene fluoride ("PVDF") or other piezoelectric polymer, co-polymer, or composite. Desirably, the ultrasonic transducer is a high-frequency transducer, capable of operating efficiently at frequencies of 10 MHz or more, preferably 20 MHz or more, more desirably 50 MHz or more.

As discussed further below, the drive circuit 58 is arranged to excite the transducer 47 to emit ultrasound and to receive electrical signals generated by the transducer responsive to ultrasound impinging on the transducer.

The transducer and optical elements of the device, including the diffuser 36 and the aperture 40 are arranged so that at least part of the region exposed to ultrasonic energy from the transducer lies within the region exposed to light supplied by the optical elements. In the particular arrangement shown, the transducer and is coaxial with the optical elements. The optical elements are arranged to apply light to a circular region of the cornea surrounding the central axis 33 of the device, and the ultrasonic transducer is arranged to apply ultrasound to a circular region surrounding the same axis.

The particular transducer shown in FIG. 1 may be as described in International Publication No. WO 2015/200817, published 30 Dec. 2015 ("The '817 Publication"), the disclosure of which is hereby incorporated by reference herein. Other structures may incorporate other types of ultrasonic transducers such as ceramic piezoelectric transducers. Also, the device may incorporate a plurality of transducers.

The drive circuit 58 (FIG. 1) includes conventional components for generating high-frequency electrical signals and supplying the same to the transducer. The drive circuit also includes conventional components for receiving electrical signals from the transducer and providing representations of those signals. For example, the drive circuit may include components such as analog to digital converters, digital to analog converters, an oscillator, amplifiers, and filters.

A control circuit 60 is connected to drive circuit 58, so that the control circuit can command the drive circuit and transducer to apply ultrasound and so that the control circuit can receive representations of signals generated by the transducer responsive to ultrasound impinging on the transducer. The control circuit 60 is also connected to light source 48 so that the control circuit can control operation of the light source. The control circuit may include a general-purpose computer having elements such as a processor, a memory linked to the processor and input/output elements as, for example, human interface elements such as a display screen and keyboard, as well as elements arranged to interface with the drive circuit 30. The memory desirably stores instructions operative to cause the computer to execute the operations discussed below. The memory may include elements storing such instructions in non-transitory form.

When the device 30 is disposed on the eye in the operative position shown in FIG. 1, there is a space 62 between the anterior surface 66 of the cornea 38 and the inner surface 37 of the diffuser. This space 62 desirably is kept filled with a liquid during operation of the device. The liquid desirably is transparent to the light such as UV that will be applied by the device, and desirably has acoustic impedance reasonably close to that of the diffuser 36 and the cornea 38. The liquid has a known, and desirably constant, speed of sound. For example, an aqueous liquid such as a saline solution or the subject's natural tears may fill the space. Alternatively, the liquid may include a perfluorocarbon adapted to supply oxygen to the cornea as disclosed in International Publication No. WO 2016/106217, the disclosure of which is hereby incorporated by reference herein.

In a method according to one embodiment of the invention, the eye desirably is exposed to a liquid containing a photoactivated crosslinking agent such as riboflavin so that the crosslinking agent penetrates into the cornea. Structure 30 is disposed on the eye of a subject prior to crosslinking treatment, and space 62 between the structure and the cornea is filled with the liquid discussed above. After placement of the device, control circuit 60 actuates transducer 47 to direct pulses of monitoring ultrasonic energy inwardly toward the eye along the axis, and to detect pulses of reflected ultrasonic energy arriving at the transducer. Each pulse of monitoring ultrasound passes inwardly toward the eye, through the diffuser 36 and through the liquid. A reflected pulse is generated at each interface between propagation media having different acoustic impedances. The magnitude of the reflected pulse will depend on the difference between the acoustic impedances of the media, as further discussed below. For example, an anterior reflected pulse arises at the interface between the liquid in space 62 and the anterior or outward-facing surface 66 of the cornea. The reflected pulse passes back through the liquid in space 62 and back through the diffuser to transducer 47. In response to the reflected pulse impinging on the transducer, the transducer generates electrical signals that are forwarded to control circuit 60. The control circuit determines the interval between emission of the monitoring pulse and return of the reflection. This interval is equal to the time of flight of the ultrasound from the transducer 47 to the anterior surface 66 and back again. As the time of flight is equal in both directions, the control circuit can divide this time by 2 to yield the time of flight of the reflected pulse from the anterior surface 66 of the cornea to the transducer 47. The time of flight of the reflected pulse through the diffuser and any other elements of the device intervening between the transducer and the interior surface 37 of the diffuser is known from the known thickness and known speed of sound in the materials of the device. The time of flight $T_1$ between the anterior surface 66 of the cornea and the interior surface 37 of the diffuser is referred to herein as the "anterior time of flight." $T_1$ is obtained by subtracting the known time of flight between the transducer 47 and the interior surface 37 of the diffuser from the time of flight from the anterior surface 66 of the cornea to the transducer 47. The speed of sound $r_{62}$ in the liquid within space 62 is also known, and hence the anterior distance $D_1$ along axis 33 between the interior surface of the diffuser and the anterior surface of the cornea is determined according to Equation 1 below:

$$D_1 = T_1/r_{62}. \quad \text{(Equation 1)}$$

A further reflected pulse, referred to herein as the posterior surface reflected pulse, occurs at the posterior surface 63 of the cornea, at the interface between the cornea and the aqueous humor in the anterior chamber of the eye. The control circuit 60 measures the time of flight $T_2$ through the cornea by timing an interval from the first anterior surface reflected pulse to the posterior surface reflected pulse and dividing the duration of this interval by 2. At this stage, prior to corneal crosslinking, the cornea is assumed to have the physical properties of the normal, untreated cornea, and the average speed of sound $r_{38}$ between the anterior and posterior surfaces of the cornea 38 is taken as equal to the published value used in normal pachymetry practice. Thus, the control circuit determines the thickness $D_2$ of the cornea is calculated as:

$$D_2 = T_2/r_{38}. \quad \text{(Equation 2)}$$

The value of $D_2$ determined at this stage of the process, prior to irradiation, is referred to herein as a reference value or pre-treatment value.

A third reflection arises at the anterior surface 72 of the lens 74 of the eye. The control circuit determines the time of flight $T_3$ between the anterior surface 72 of the lens and the posterior surface 63 of the cornea by measuring the interval between receipt of the posterior surface reflected pulse from surface 66 and the receipt of the reflected pulse from surface 72 and dividing by 2. The speed of sound $r_{70}$ in the aqueous humor within anterior chamber 70 is a known constant. Thus, the control circuit determines the $D_3$ between the posterior surface 63 of the cornea and the anterior surface 72 of the lens according to Equation 3 below:

$$D_3 = T_3/r_{70}. \quad \text{(Equation 3)}$$

The control circuit may actuate the transducer to perform the measurements described above once, or may repeat these measurements one or more times and select a value for each of $D_1$, $D_2$, and $D_3$ by techniques such as averaging with or without discarding outlying values. Once the values of these distances have been determined, the control circuit computes the distance $D_0$ between the inner surface 37 of the diffuser and the anterior surface of the 72 of the lens according to Equation 4:

$$D_0 = D_1 + D_2 + D_3 \quad \text{(Equation 4)}$$

$D_0$ is a distance between a reference location (the interior surface 37 of the diffuser) anterior to the cornea and a structure of the eye (the surface 72 of the lens) that is posterior to the cornea. This distance $D_0$ is also referred to herein as a "reference distance." Because the reference location is carried on structure 30, which rests on the eye, this distance $D_0$ remains substantially fixed. Changes in the focus of the lens 74, commonly referred to as "accommodation," can alter the shape of the lens and thus alter $D_0$. One or more drugs that temporarily suppress accommodation may be administered locally to the treated eye or systemically before the procedure.

After $D_0$ has been determined, the control circuit actuates light source 48 to apply ultraviolet light to irradiate the cornea. As described in greater detail in the aforementioned '054 Publication, the light passes from the light source and into diffuser 36 from the periphery of the diffuser. Light scattered by the diffuser irradiates the cornea and causes crosslinking within the cornea. This crosslinking changes the elastic modulus of the cornea and changes its thickness. Some reshaping of the cornea also occurs during irradiation, although further reshaping typically will occur over days or weeks following irradiation. Thus, after irradiation, the anterior and posterior surfaces of the cornea can be displaced from their original locations to new locations indicated by broken lines at 66' and 63' respectively in FIG. 2. Control circuit 60 actuates the transducer 7 to apply monitoring pulses of ultrasound, to detect reflections from anterior and posterior surfaces 66' and 63' of the cornea, and from anterior surface 72 of the lens. The anterior distance $D_1'$ between the reference location (surface 37 of the diffuser) and anterior surface 66' is determined in the same manner as $D_1$ discussed above. The posterior distance $D_3'$ is determined in the same manner as $D_3$ discussed above. Because the elastic modulus of the cornea has been altered to an unknown degree by the crosslinking process, the speed of sound $r_{38}$ within the cornea is not known at this time, and hence the thickness $D_2'$ of the cornea cannot be determined accurately based on time of flight through the cornea, as by using Equation 2 above. However, the measurement of the anterior and posterior distances $D_1'$ and $D_3'$ is not affected by the speed of sound within the cornea, and $D_0$ is constant. Thus, the control circuit determines the corneal thickness D2' by subtraction according to Equation 5 below:

$$D_2' = D_0 - (D_1' + D_3') \quad \text{(Equation 5)}$$

The control circuit desirably repeats the determination of the corneal thickness $D_2'$ at several times during the treatment. The control circuit may control the operation of the light source 48 based in whole or in part on the measured corneal thickness $D_2'$. For example, the control circuit may terminate operation of the light applying source when a difference between the pre-treatment corneal thickness $D_2$ measured prior to irradiation and a measured corneal thickness $D_2'$ measured during the irradiating step reaches a predetermined threshold. The threshold may be a function of the pre-treatment corneal thickness $D_2$ as, for example, a percentage of the pre-treatment value. Stated another way, the change in corneal thickness is correlated with the degree of crosslinking achieved by the irradiation step, so that the corneal thickness serves as a proxy for the degree of crosslinking.

The corneal thickness $D_2'$ measured in this manner also can be used to determine the speed of sound in the cornea during the treatment. To do so, the control circuit determines the time of flight of ultrasound through the cornea by timing an interval between arrival of the reflection from the anterior surface 66' of the cornea and arrival of the reflection from posterior surface 63' of the cornea. The control circuit then divides the thickness of the cornea by the measured time of flight. The speed of sound in the cornea is directly related to the elastic modulus of the cornea, and therefore the speed of sound also can be used as a proxy for the degree of crosslinking.

Figure 3:
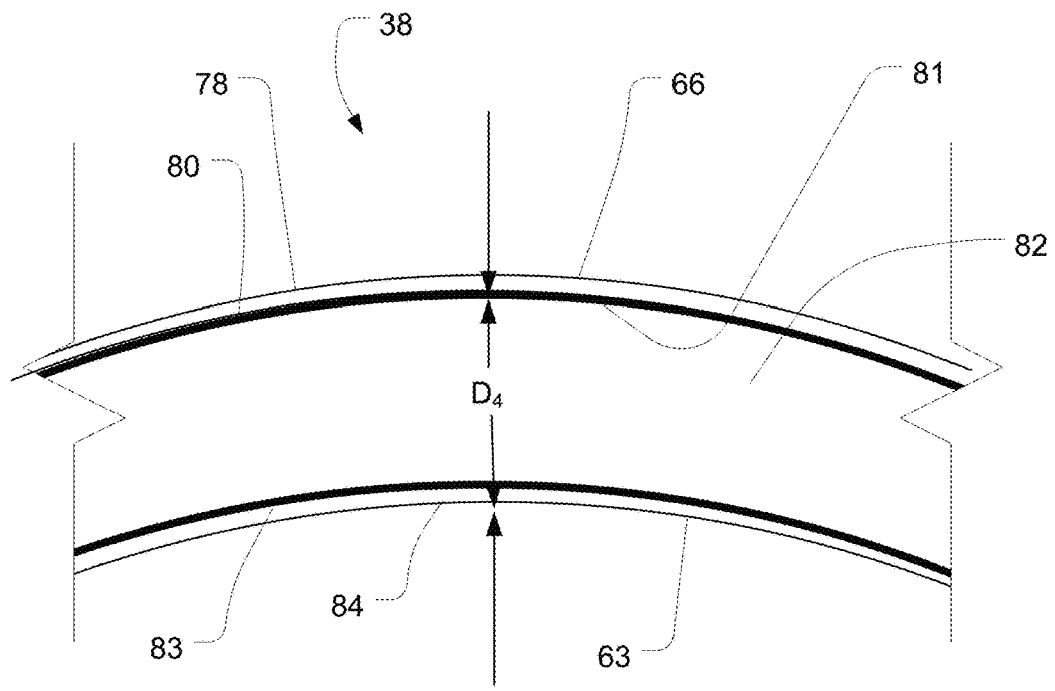
FIG. 3 is a diagrammatic sectional view of a cornea prior to corneal crosslinking.

In the embodiment discussed above, the cornea 38 is treated as a unitary structure, and the thickness of the entire structure is measured before and during irradiation. However, the cornea includes distinct layers. As shown in FIG. 3, depicting a cornea prior to irradiation and crosslinking, these layers include epithelium 78 at the anterior surface 66; a layer 80 of tissue referred to as "Bowman's layer" immediately posterior to the epithelium; the stroma 82 posterior to Bowman's layer, a further layer 83 referred to as "Descemet's membrane," and endothelium 84 at the posterior surface 63 of the cornea. The interfacial surfaces of these layers also give rise to reflections of the monitoring ultrasound that are ignored in the embodiment discussed above. The control circuit may use techniques commonly used in ultrasonic ranging to ignore irrelevant reflections. For example, the control circuit may be set to ignore signals representing reflected ultrasound that arrives at the transducer during intervals that do not correspond to the expected time of arrival of reflections from the surfaces of interest.

In a further embodiment, the control circuit actuates the transducer to determine the thickness D4 (FIG. 3) of a structure of the cornea that includes stroma 82 and the layers posterior to the stroma, but excludes the epithelium 78. In this embodiment, the control circuit acquires signals representing the reflection from the interfacial surface forming the anterior surface 81 of the stroma 82, along with signals representing reflections from the posterior surface 63 of the cornea and from the lens of the eye (not shown). The pre-treatment value of D4 is determined in the same way as the pre-treatment value of D2, based on the difference in time of flight of the reflections from surfaces 81 and 63 and known pre-treatment properties of the layers in the cornea. The anterior distance from the reference location on the device 30 resting on the eye (FIG. 1) to the anterior surface 81 of the stroma is determined in the same manner as $D_1$ discussed above. The posterior distance between the posterior surface 63 and the lens of the eye is also determined in the same manner discussed above. Here again, the reference distance from the reference point on structure 30 to the lens is simply the sum of the anterior distance, the posterior distance and the thickness D4 of the corneal structure. In the same manner as discussed above, values of the anterior distance and posterior distance are measured again during the irradiation step and subtracted from the reference to yield the thickness D4' of the corneal structure during irradiation.

Figure 6:
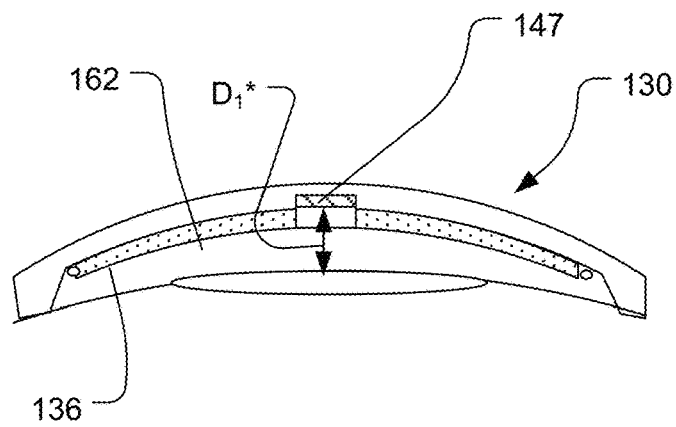
FIGS. 6, 7, and 8 are diagrammatic cross-sectional views depicting devices in accordance with further embodiments of the invention.
Figure 7:
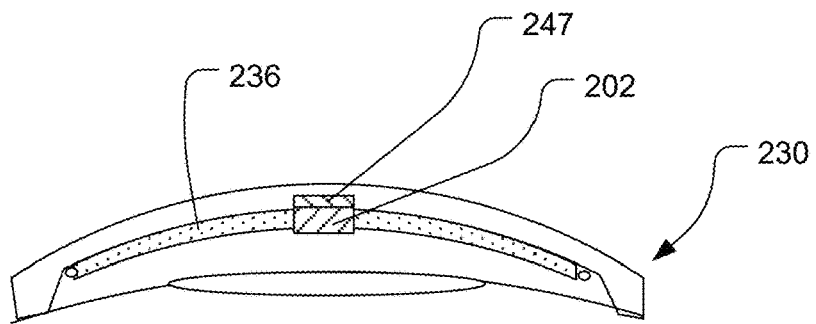
Figure 8:
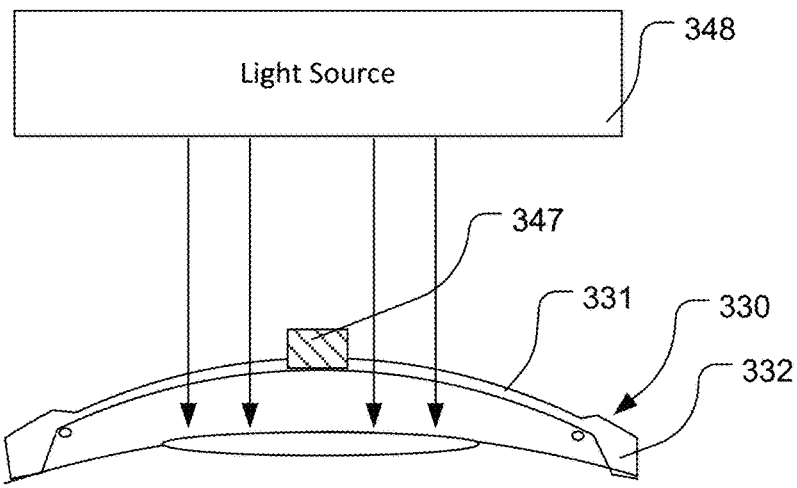

In the embodiment of FIGS. 1 and 2, the interior surface of the diffuser serves as a reference location for distance measurements. In other embodiments, other elements of the device may serve as the reference location. For example, a device 130 shown in FIG. 6 is similar to the device 30 discussed above, except that device 130 has a hole 101 in the diffuser 136. This hole is aligned with the ultrasonic transducer 147, so that the transducer is in direct contact with the liquid in the space 162 between the device and the eye. In this embodiment, the transducer 147 serves as the reference location. In a further embodiment (FIG. 7), the device 202 includes a clear polymeric lens 202 extending through the diffuser 236 in alignment with the ultrasonic transducer 247, so that ultrasound is transmitted between the liquid in space 262 and the transducer through the lens. In this embodiment, a surface of the lens may serve as the reference location. Also, in the embodiments disclosed herein, distances measured with respect to a particular reference location on the device may be transposed to distances relative to another reference location on the device, based on the known geometry of the device. Further, the control circuit may use mathematical calculations equivalent to the particular calculations discussed herein as, for example, by performing calculations in different order than discussed above. Also, the device need not incorporate a diffuser and fiber optic as discussed above. For example, a device 330 shown in FIG. 8 includes a body 332 arranged to rest on a surface of the eye during use and to support an ultrasonic transducer 347. The body has a region 331 transparent or translucent to ultraviolet radiation, so that ultraviolet light from a light source 348 such as a laser disposed remote from the eye can be transmitted through the ambient environment through region 331 of the body and through the space 362 between the body and the eye.

During irradiation, the position of the cornea typically shifts as the collagen shrinks. As best seen in FIG. 1, the cornea is generally in the form of a dome, with the edges of the dome being held in substantially fixed position by the sclera 34 of the eye. As crosslinks form, the center of the cornea tends to shift in the posterior direction.

In yet another embodiment of the invention, this effect is measured by monitoring the position of the cornea relative to a reference location having a position fixed to the eye. As discussed above, the structure desirably rests on the eye and thus elements of the structure such as the transducer and the diffuser can serve as reference locations. For example, the position of the cornea along the anterior-to-posterior axis is represented directly by the anterior distance from the anterior surface of the cornea to the reference location, such as $D_1$ and $D_1'$ shown in FIG. 2. Likewise, the posterior distance between the cornea and an element of the eye posterior to the cornea, such as $D_3$ and $D_3'$ changes as the position of the cornea shifts. Measurement of the posterior distance in FIG. 2 uses the surface of the lens as the reference location for measuring the position of the cornea. Either distance can be used as a proxy for the degree of crosslinking Where the reference location used to monitor the position of the cornea is the lens or another element of the eye itself, there is no need for an ultrasonic transducer used to measure the position of the cornea to be in a fixed position relative to the eye. In still other embodiments, measurements other than ultrasonic measurements can be used to determine the position of the cornea. For example, optical measurements using light reflected from the anterior surface of the cornea can be used.

In the embodiments discussed above, the lens of the eye is an element of the eye posterior to the cornea that acts as a reflector for ultrasound and as a reference location for determining the posterior distance such as $D_3$ and $D_3'$. In other embodiments, other elements of the eye such as the retina (not shown) at the rear of the eye or the iris 71 may be used instead of the lens. For example, the monitoring ultrasound may be directed along an axis oblique to the central axis 33 of the eye so that ultrasound passing through the cornea will be reflected from the iris.

Figure 4:
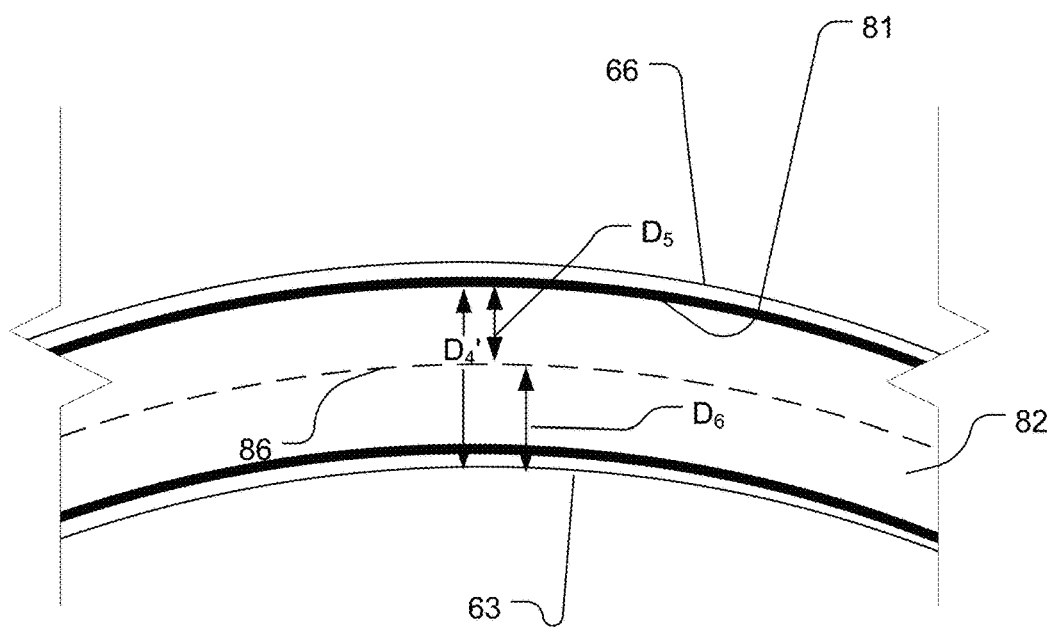
FIG. 4 is a diagrammatic sectional view similar to FIG. 3 but depicting the cornea after corneal crosslinking.

During corneal crosslinking, a surface of demarcation 86, depicted in broken lines in FIG. 4, forms within the stroma 82. Although the present invention is not limited by any theory of operation, it is believed that this surface of demarcation represents a boundary between a more crosslinked region adjacent the anterior surface 81 of the stroma and a less crosslinked region adjacent the posterior surface of the stroma. More highly crosslinked corneas have the surface of demarcation in more posterior positions than less fully crosslinked corneas. In a further embodiment, the control circuit determines the location of surface of demarcation 86 in the anterior-to-posterior direction. The location of this surface may be used as a proxy for the extent of crosslinking, and the control circuit may control operation of the light source responsive in part or in whole to this proxy. Desirably, the location of surface 86 is determined relative to a naturally occurring surface of the cornea. For example, the transducer may be actuated to direct monitoring ultrasound into the eye, detect reflections from the surface 86 and from another surface of the cornea, and measure the interval between arrival of these reflections at the transducer. For example, the interval between arrival of reflections from anterior surface 81 of the stroma and from surface 86 is directly related to the distance $D_5$ between these surfaces, and thus directly related to the extent of crosslinking. In another example, the system may measure distance D6 between surface 86 and the posterior surface 63 of the cornea; this distance diminishes with increasing crosslinking Reflections from other surfaces of the cornea that reflect ultrasound can be used in conjunction with reflections from the surface of demarcation in a similar manner.

As discussed in the '817 Publication incorporated by reference herein, a force applied to the cornea in the posterior direction will momentarily displace the center of the cornea. When the force is released, the cornea will rebound and vibrate at a resonant frequency. As pointed out in the '817 Publication, the resonant frequency is related to the degree of crosslinking achieved by the process and can be used as a proxy for the degree of crosslinking. For example, a change in the resonant frequency from a baseline resonant frequency before crosslinking can be used. Thus, the '817 Publication teaches that a control system can control operation of the light source used in crosslinking based in whole or in part on the resonant frequency monitored during crosslinking. In certain embodiments, the '817 Publication teaches monitoring the frequency or period of the vibrations after application of a mechanical force to the cornea by applying a powerful excitation pulse of ultrasonic energy, also referred to as a "push pulse." The '817 Publication further teaches determining the resonant frequency or period of the cornea by applying monitoring ultrasound and determining the interval between maxima or minima in the Doppler shift of ultrasound reflected from the cornea.

Figure 5A:
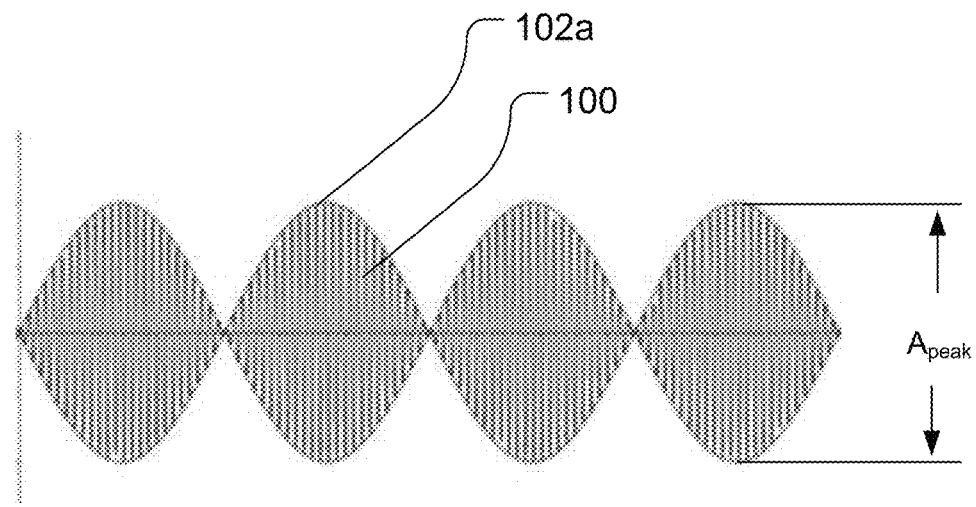
FIGS. 5A-5C are diagrammatic representations of waveforms used in certain embodiments of the invention.
Figure 5B:
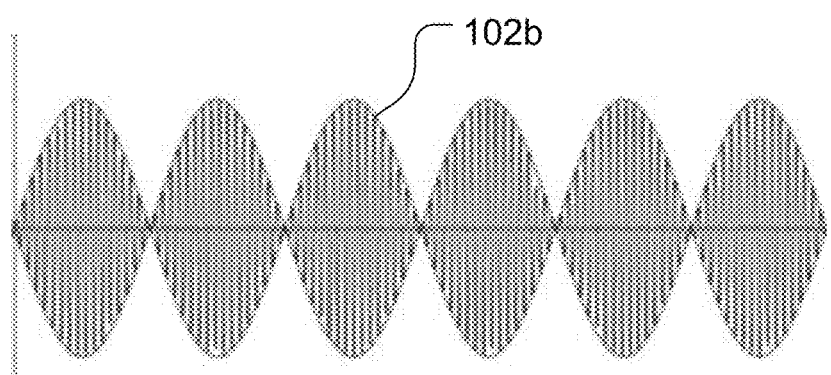
Figure 5C:
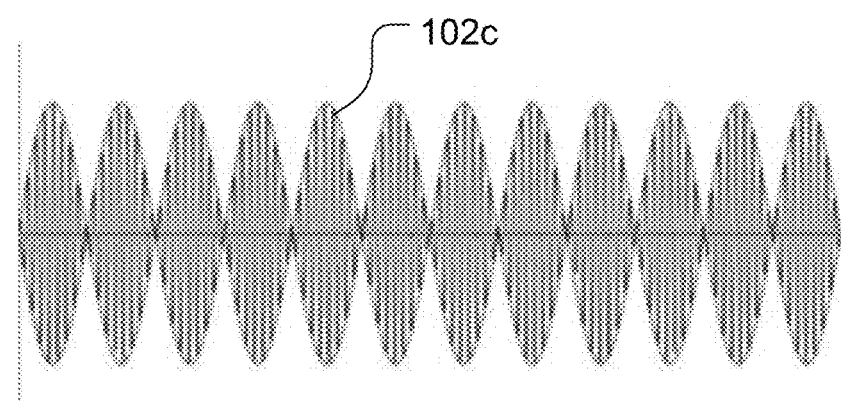

In a further embodiment of the present invention, structure 30 is positioned on the eye as discussed above with reference to FIG. 1, and here again the space 62 between the structure and the cornea is filled with a liquid as discussed above. To measure the resonant frequency of the cornea, control circuit 60 commands drive circuit 58 to apply a succession of push pulse drive signals to transducer 47. The drive signal for each push pulse includes an alternating carrier signal at an ultrasonic frequency that typically is in the MHz frequency range. This carrier signal is amplitude-modulated by a modulation signal at a modulation frequency that is in the range corresponding to the range of resonant frequencies of the cornea, which typically are below 1 KHz and most typically below 400 Hz. FIG. 5A schematically depicts a carrier signal 100 amplitude-modulated with a modulation signal 102a. In this figure, the frequencies of the carrier signal and modulation signal are not drawn to scale. The carrier signal varies from zero amplitude to a peak amplitude $A_{peak}$, and such variation occurs at the modulation frequency. FIG. 5B depicts the same carrier signal 100 modulated with a modulation frequency 102b higher than frequency 102a. FIG. 5C shows the same carrier signal 100 modulated by a still higher modulation frequency 102c. Transducer 47 emits ultrasound at the carrier signal frequency, amplitude modulated at the modulation frequency. The drive signal for each push pulse is amplitude modulated at a single modulation frequency. The control circuit varies the modulation frequency so that different push pulses have different modulation frequencies. Desirably, all of the push pulses in a series of push pulses have the same peak amplitude $A_{peak}$.

As the ultrasound impinges on the cornea, it applies a force to the cornea in the posterior direction. This force varies with the amplitude of the ultrasonic waves in the push pulse, and thus varies at. This varying force excites vibration of the cornea. The amplitude of vibration of the cornea excited by a push pulse will be greater if the modulation frequency of the push pulse is close to a resonant frequency of the cornea and lower if the modulation frequency is far from a resonant frequency of the cornea.

The control circuit also actuates the drive circuit 58 and transducer 47 to emit monitoring ultrasound and to monitor ultrasound reflected from the cornea. For example, the monitoring ultrasound may be emitted as a series of monitoring pulses during each interval between successive push pulses. The ultrasound reflected from the cornea impinges on the transducer so that the transducer produces signals representing the reflected ultrasound. The reflected ultrasound from each monitoring pulse has a frequency corresponding to the frequency of the monitoring ultrasound, plus or minus a Doppler shift caused by movement of the cornea towards or away from the transducer. The Doppler shift is directly proportional to the velocity of this movement, referred to as the rebound velocity, at the instant the monitoring pulse impinges on the cornea. The maximum magnitude of the Doppler shift observed for any of the monitoring pulses following after a push pulse represents the maximum rebound velocity generated by that push pulse. The control circuit compares the maximum rebound velocities generated by the various push pulses in a sequence of push pulses with one another, and selects the push pulse that generates the greatest rebound velocity. The modulation frequency applied during that push pulse is taken as an estimate of a resonant frequency of the cornea. Stated another way, in this embodiment, the control circuit varies a modulation frequency of the force applied to the cornea over a range of frequencies and estimates the resonant frequency based on the rebound velocity elicited by the various frequencies within the range. The resonant frequency determined in this manner will vary with the degree of crosslinking and thus may serve as a proxy for the degree of crosslinking Thus, the control circuit may determine a baseline value of the resonant frequency prior to irradiation of the cornea and may repeat this determination during the irradiation and crosslinking process to acquire additional values. Here again, the control circuit may control operation of the light source responsive in whole or in part to the resonant frequency.

Typically, the cornea exhibits several resonant frequencies. As described in Acka et al., Observation of sound-induced corneal vibrational modes by Optical coherence tomography, BIOMEDICAL OPTICS EXPRESS Vol. 6, No. 9 (2015), pp. 3313-19 ("Acka et al"), the disclosure of which is hereby incorporated by reference herein, these modes include a fundamental or [0,1] mode; a [0,2] mode, and a [0,3] mode. These modes have different resonant frequencies. One or more of the resonant frequencies may be used as the proxy for control of the irradiation process. A series of push pulses used to determine each resonant frequency will include push pulses having a range of modulation frequencies encompassing the expected value of that resonant frequency.

A finite time is required to emit the various push pulses and monitoring pulses used to determine a resonant frequency. In theory, the properties of the cornea may change during this time as crosslinking continues. However, this is of little practical effect. Typically, the crosslinking process occurs over a period of tens of minutes, whereas the time required to determine a resonant frequency typically is a fraction of a second. Thus, any change in the properties of the cornea during the time required to determine a resonant frequency will be insignificant. The relatively small distance between the structure and the eye, typically on the order of 1 mm or less, results in very short times of flight for ultrasound passing between the structure and the cornea, and facilitates application of numerous monitoring pulses during each interval between push pulses. In a further variant, the series of push pulses may include plural push pulses having the same modulation frequency, and a sampling interval may include plural intervals between push pulses having the same modulation frequency. The timing relationship between the monitoring pulses and the push pulses may be varied for these different intervals. This allows acquisition of velocity data, position data, or both at numerous times after termination of the preceding push pulse.

In a further embodiment, the cornea is excited by a series of push pulses with different modulation frequencies as described above. Here again, the control circuit actuates the drive circuit and transducer to emit a series of monitoring ultrasound pulses as described above, so that reflected ultrasound from the cornea impinges on the transducer and the transducer generates electrical signals responsive to the reflected pulses. The control circuit monitors the arrival time of the reflected pulses so as to determine the time of flight of each reflected pulse and thus determine the position of a surface of the cornea relative to a reference location on device 30 at the instant the pulse is reflected. For example, where the reflections from the anterior surface of the cornea are used, the system repeatedly measures $D_1'$ as discussed above with each monitoring pulse. In a further variant, the system may repeatedly measure the posterior distance $D_3'$. The control circuit takes a rest-position measurement using one or more monitoring pulses before application of a push pulse, as well as a series of measurements during each interval between push pulses. The control system compares the measurements during a sampling interval between push pulses with the rest-position measurement, so as to determine the displacement of the cornea from the rest position at a series of times during the interval following each push pulse. The control circuit determines the maximum displacement of the cornea and selects the modulation frequency of the push pulse that yields the maximum displacement as the best estimate of the resonant frequency of the cornea. In yet another variant, the monitoring pulses may be used to measure the thickness $D_2'$ of the cornea as discussed above, both at rest and following application of a push pulse. By comparing the thickness immediately following application of a push pulse with the thickness measured at rest, the control system can determine the compression induced by the push pulse. The compression may be used as a further proxy for degree of crosslinking.

The embodiments discussed above may be varied in many ways. For example, the force that excites the cornea need not be applied by ultrasonic push pulses, and the displacement or velocity of the cornea can be measured by techniques other than ultrasonic monitoring pulses as, for example by optical techniques. In one such approach, the force that excites the cornea can be applied by acoustic waves in the audible range, and the frequency of such acoustic waves can be swept over the range of frequencies encompassing the expected resonant frequency of the cornea. Such acoustic waves can be provided by a source remote from the eye and may be transmitted through the air to the eye. However, the required acoustic waves are in the low audible frequency range, and typically must be quite loud (as, for example, about 100 dB) for effective excitation. Transmission of these waves through the ambient air in the vicinity of a living patient is generally not desirable. In a variant of this approach, a parametric array is used to generate ultrasonic waves at frequencies above the audible range but low enough to propagate in air, and to direct these waves through the air so that they combine with one another at or near the anterior surface of the cornea to form the desired audible frequency sonic waves that excite the cornea. This approach allows excitation of the cornea by a device remote from the eye without exposing the patient and medical personnel to undesirably loud sound levels. By adjusting the frequencies of the ultrasonic waves, the frequency of the audible waves, and thus the frequency of the force applied to the cornea, can be varied.

As discussed above, ultrasonic monitoring pulses can be used to monitor the instantaneous position of the cornea or the instantaneous velocity of the cornea after application of push pulses. For velocity measurement using the Doppler effect, it is generally desirable to use monitoring pulses created by driving the transducer with several cycles of a fixed frequency-alternating signal. The resulting narrow band tone provides accurate frequency domain resolution, which is needed to resolve small Doppler shifts. For position measurement, the monitoring pulses desirably are extremely broad band, meaning they are very short in time. This allows accurate time domain positional (determined by time of flight) resolution. These types of pulses are typically generated by a damped ultrasound transducer excited with a single, very rapid, voltage spike.

In a further variant, the system can acquire both instantaneous position and instantaneous velocity of the cornea. One method is to use the same monitoring pulse to do both measurements. The bandwidth of the monitoring pulse desirably is balanced between the narrow band desirable for Doppler shift resolution and the broad band desirable for range resolution. In a further variant, only the front edge of the pulse reflected by the cornea is used for position detection, which can allow use of a narrower band for this combination" monitoring pulse than would otherwise be usable for position measurement. Another method of collecting both velocity and position data during a single period between push pulses is to use two different types of monitoring pulses, i.e., broad band position-measuring pulses and narrow band Doppler velocity-measuring pulses. By delivering the two types of monitoring pulses very close in time to each other, there will only be a very small error between the measured position of the cornea and the position where it was located when a pulse bounced off its surface. Because the device 30 positions the transducer close to the cornea, it facilitates use of monitoring pulses in close succession.

In the embodiments discussed above, the instantaneous corneal position or velocity data acquired during intervals between push pulses is used to determine the resonant frequency of the cornea. However, this data can be used in other ways. For example, using both instantaneous position and instantaneous velocity allows the control system to construct a map of position and velocity versus time following the application of a push pulse. Such a map identifies properties of the cornea that change with crosslinking, and thus can be used as proxies for the degree of crosslinking to control the irradiation process. A baseline map may be acquired prior to irradiation and crosslinking, and additional maps may be acquired during the irradiation step. Here again, the irradiation step may be terminated when the change additional maps indicate that the required degree of crosslinking has occurred.

In a further embodiment, the magnitude of the corneal displacement responsive to a push pulse, or the magnitude of the corneal rebound velocity responsive to a push pulse, may be used as a proxy for the degree of crosslinking. For example, as the elastic modulus of the cornea increases, the cornea becomes stiffer, so that a given force will cause less displacement. A simplified representation of the displacement of the cornea caused by a push pulse is given by Equation 6 below:

$$F = kx \qquad \text{(Equation 6)}$$

where F is the applied force in the posterior direction, k is a spring constant, and x is the displacement caused by the push pulse. An increase in elastic modulus of the cornea tends to increase the spring constant k. Using this model, if the same force F is applied to the cornea before irradiation and during irradiation, the change in the spring constant k can be determined by comparing the displacement x during irradiation with the baseline displacement before irradiation.

However, even where ultrasonic push pulses are applied with the same amplitude and modulation frequency before and during irradiation, the force F to the cornea changes, because changes in the properties of the cornea cause changes in the reflection and attenuation of ultrasound by the cornea. The force F applied by a push pulse is represented by Equation 7 below:

$$F = F_P + F_A \quad \text{(Equation 7)}$$

in which Fp represents radiation pressure governed by Newton's 3rd law, as the reflected pulse rebounds off the cornea and $F_A$ represents force resulting from attenuation within the cornea. FA is given by:

$$F_A = 2aI/c \quad \text{(Equation 8)}$$

Where a is the attenuation in the tissue, I is the intensity of the acoustic field and c is the speed of sound in the tissue. As the reflection of ultrasound at the surface of the cornea increases, the force applied to the cornea by a given push pulse will increase. Also, as the attenuation of ultrasound passing through the cornea changes, the force applied by a given push pulse will change.

To assess the change in the reflection at the surface that contributes the radiation pressure component of F', the acoustic impedance of the cornea must be determined, as mismatches in acoustic impedance cause reflections for propagating waves. Acoustic impedance (Z) is the product of the density ($\rho$) and the speed of sound (c), i.e., $Z=\rho c$. As discussed above with reference to FIGS. 1 and 2, the thickness of the cornea can be measured during irradiation. An assumption can be made that the corneal dimensions are only changed in the thickness direction due to thinning induced by crosslinking, and the change in corneal volume can be calculated based on the change in thickness alone. Alternatively, the change in the position of the cornea, such as that measured by the change in D1' discussed above with reference to FIG. 2, which represents flattening of the corneal dome, can be used in addition to the change in thickness to more precisely calculate the change in the volume of the cornea so as to take into account change in dimensions of the cornea in directions transverse to the axis. Because the mass of the cornea does not change appreciably during crosslinking, the density of the cornea can be calculated based on the change in volume. As also discussed above, the speed of sound in the cornea (c) can be determined based on time of flight through the cornea and the known thickness of the cornea. The same calculations can be performed for the cornea stroma if desired. The calculated speed of sound and density can be used to calculate the acoustic impedance of the cornea during irradiation, designated Z'. The acoustic impedance Z of the cornea prior to irradiation can be determined based on similar measurements or derived from published values for physical constants of normal corneal tissue. The reflection coefficients at the interface between the cornea and liquid contact with the anterior surface of the cornea can be calculated before (R) and after (R') irradiation by Equations 9 and 10 below, where "Zwater" represents the acoustic impedance of the liquid disposed between the structure 30 and the eye, which is typically close to that of water.

$$R = \left[\frac{Z_{cornea} - Z_{water}}{Z_{cornea} + Z_{water}}\right]^2 \quad \text{(Equation 9)}$$

$$R' = \left[\frac{Z'_{cornea} - Z_{water}}{Z'_{cornea} + Z_{water}}\right]^2 \quad \text{(Equation 10)}$$

With the difference in the reflection at this boundary known, the change in contribution of the radiation pressure to the push force is known. This tends to increase as irradiation and crosslinking proceed, as the higher speed of sound in the cornea and higher density yield a higher acoustic impedance. Since the impedance of cornea is already higher than the water in front of it, an increase in Z increases the size of the reflection, adding more force to the push.

To assess the change in the attenuative radiation force component of the push force ($F_A$), the change in attenuation within the cornea as a result of crosslinking must be taken into account. This can be done using the amplitude of ultrasound reflected from the posterior surface of the cornea. Making again the underlying assumption that the geometry of the system remains substantially unchanged (i.e., the angle of the incident waves onto the cornea is roughly normal and unchanged before and throughout the CXL therapy), the now known reflection coefficients at the front and back surfaces of the cornea can be used to predict the expected amplitude of the retuning echo from the back surface. Any small differences in geometry of the system as a function of curvature changes resultant from non-thickness related changes to D1 and D3 can additionally be compensated for through simple geometry assuming an incident ultrasonic plane wave and a hemispherical corneal surface. With the differences in transmission and reflection accounted for, any remaining difference between these echo amplitudes before and after CXL is attributable to increased attenuation in the tissue.

The push force, F', applied to the cornea by the push pulses after CXL commences is now known relative to the baseline push force F. Any measured changes in the deflection of the cornea as a result of the push pulses is normalized to the actual applied force, yielding deflection measurements that are direct proxies of the material properties of the cornea. The same approach can be used to normalize rebound velocity measurements.

In the embodiments discussed above, one or more measured parameters of the cornea, or of a corneal structure such as the stroma, are used as proxies for material properties of the cornea and hence as proxies for the degree of crosslinking, and are used by the control system to control operation of the light source. A baseline response determined prior to irradiation is a proxy for the original material properties, whereas each additional response is a proxy for the material properties at a time during irradiation. Comparison of the proxy determined during irradiation with the original or baseline proxy gives an indication in the change in material properties, and thus an indication of the degree of crosslinking that has occurred. It is not essential to determine the actual material properties. Moreover, where the same transducer or transducers mounted on the same structure resting on the eye are used for both baseline and additional measurements, the same errors will affect both baseline and additional measurements. Therefore, these errors will be substantially canceled in the comparison between the baseline and additional proxies.

In the embodiments discussed above, the various proxies for degree of crosslinking have been referred to separately. However, two or more of the various proxies can be used in combination with one another to provide a composite proxy that can be used in the same manner.

A further embodiment of the invention uses measured parameters of the cornea in conjunction with a finite element model of the eye to control operation of the light source during crosslinking. As is known in the art, a finite element model (FEM) of the eye, uses known or assumed fundamental materials properties such as elastic moduli, density, and the like at various discrete points in mesh configuration that defines a 2-dimensional slice or a 3-dimensional solid model of the actual cornea or of the eye as a whole. This model is then used to simulate the shape the cornea is expected to assume over the weeks following the crosslinking procedure as a response to changes in the fundamental materials properties that are expected to occur in a crosslinking process. The expected changes in fundamental materials properties can be changed so as to arrive at materials properties that will yield the desired shape of the cornea after crosslinking.

One example of a method according to this aspect of the invention uses a 3-dimensional FEM approach. The shape of the cornea to be treated is modeled with a network of discrete points determined before the procedure by measuring the topography (front and back surface) of the cornea using standard corneal topographic measurement systems. This shape is then "meshed" in the simulation using a method common to FEM and known to those skilled in the art, creating a 3-dimensional representation of the cornea. Assumed fundamental material properties of corneal tissue are then assigned to this mesh. Some finite element approaches model the entire globe of the eye; but, to save computational time, typically only the cornea is modeled and the boundary conditions at the sclera-cornea interface are defined by assuming a standard condition commonly used in finite element models of the cornea.

Optionally, the actual cornea to be crosslinked is subjected to one or more stimuli, and the response of the cornea to these stimuli is measured to provide collect a measured "baseline" response of the cornea to these stimuli. For example, the stimuli may include application of a force to the cornea using acoustic waves or one or more ultrasonic push pulses and measuring the response of the cornea as described above or as described in the '817 Publication. This step may be performed using a structure as discussed above but without irradiating the eye. The FEM of the cornea is used to simulate the response of the cornea to the same stimuli to provide a modeled baseline response. The modeled baseline response may be evaluated against the actual measured baseline response. The assumed fundamental material properties and boundary conditions of the FEM may be adjusted within a range defined by standard variation in healthy human eye tissues until the modeled response matches the measured baseline. This helps to assure that the model more accurately represents the eye to be treated.

The FEM is used to iterate through differing amounts of corneal stiffening to be applied by the crosslinking. The FEM may also be used to iterate through different sizes and shapes of the zone of the cornea to be irradiated, i.e., different aperture sizes and shapes. The amount of stiffening is adjusted by changing the fundamental material properties in the FEM, within the range of properties attainable by corneal crosslinking. The region where such stiffening occurs is adjusted based on the simulated aperture size and shape. The model with adjusted parameters is used to predict the final corneal shape that will result from each set of simulated parameters. Once a set of post-crosslinking material properties and irradiation zone that will yield the optimum post-treatment corneal shape are selected, the response of the cornea to the stimuli is simulated using the model using the fundamental material properties in the zone to be treated, to provide a simulated post-treatment response. For example, the simulation may show that when the eye has been treated to achieve the selected fundamental material properties, the cornea will be displaced through a distance $x^*$ by an ultrasonic push pulse with a predetermined amplitude and modulation frequency.

The simulated post-treatment response becomes a control point that can be used to determine when the irradiation should be terminated during the treatment. A real stimulus that corresponds to the simulated stimulus used in deriving the simulated post-treatment response is applied to the eye during treatment, and the real response of the cornea to this stimulus is measured. When the measured response matches the simulated response, the irradiation step is terminated. In the example given above, the irradiation step may be terminated when measurement of the displacement of the using real push pulse with the predetermined amplitude and modulation frequency indicates that the displacement is equal to $x^*$.

The following paragraphs further illustrate aspects of the invention:

A method of corneal crosslinking comprising:
  (a) irradiating a cornea in an eye of a living subject with light cornea in the presence of a crosslinking agent to induce crosslinking in the cornea; and
  (b) determining a response of the cornea by
    (i) repeatedly applying pulses of excitation ultrasonic energy to the cornea so that each pulse momentarily deforms the cornea;
    (ii) applying monitoring ultrasonic energy to the cornea during monitoring intervals between pulses of ultrasonic excitation energy; and
    (iii) detecting monitoring ultrasonic energy reflected from the cornea and producing signals representing the reflected monitoring ultrasonic energy; and
    (iv) determining a value representing at least one parameter selected from the group consisting of (a) rebound velocity of the cornea; (b) displacement of the cornea from a rest position, and (c) compression of the cornea based on the signals;
  (c) controlling the irradiating step based at least in part on the value determined in step (b).

A method as recited above further comprising repeating the determining step to provide a baseline value before commencement of the irradiating step and one or more additional values during the irradiating step and comparing the additional values to the baseline response, the step of controlling the irradiating step being performed based at least in part on the results of the comparison.

A method as recited in above wherein each repetition of the determining step is performed using one or more transducers mounted on a structure resting on the anterior surface of the eye.

A method as recited in above wherein the value represents rebound velocity of the cornea and the step of determining the value includes determining a Doppler shift of the reflected monitoring ultrasonic energy.

A method as recited in above wherein the step of determining a Doppler shift includes applying monitoring ultrasonic energy in the form of discrete bursts at a plurality of different delay times after pulses of excitation ultrasonic energy and determining the Doppler shift of the reflected ultrasonic energy produced by each burst, and determining the maximum magnitude of the Doppler shift determined for bursts emitted during each monitoring interval.

A method as recited above wherein each monitoring interval encompasses a plurality of intervals between pulses of excitation ultrasonic energy.

A method as recited above wherein the value represents displacement of the cornea from a rest position and the step of determining the value includes:

(a) determining a rest-position time of flight of monitoring ultrasonic energy between a reference location and a surface of the cornea while the cornea is in the rest position, undistorted by excitation ultrasonic energy;

(b) determining a deformed-position time of flight of monitoring ultrasonic energy between a reference location and the surface of the cornea shortly after application of excitation ultrasonic energy; and (c) determining a difference between the rest-position time of flight and the deformed-position time of flight.

A method as recited above wherein the reference location is a surface of the lens of the eye of the subject.

A method as recited above wherein the reference location is a location on a structure resting on an anterior surface of the eye.

A system for corneal crosslinking comprising:

(a) a light source adapted to irradiate a cornea of an eye of a subject;

(b) one or more ultrasonic transducers (c) a drive circuit connected to the one or more transducers, the drive circuit being operable to actuate the one or more transducers to:

(i) repeatedly apply pulses of excitation ultrasonic energy to the cornea so that each pulse momentarily deforms the cornea;

(ii) apply monitoring ultrasonic energy to the cornea during intervals between pulses of ultrasonic energy; and (iii) detect monitoring ultrasonic energy reflected from the cornea and produce signals representing the reflected monitoring ultrasonic energy; and (d) a control circuit connected to the drive circuit and to the light source, the control circuit being operable to (i) determine based on the signals a value representing at least one parameter selected from the group consisting of rebound velocity of the cornea; displacement of the cornea from a rest position; and compression of the cornea and (ii) control operation of the light source based at least in part on the value.

A system as recited above further comprising a structure adapted to rest on an anterior surface of the eye and to transmit light from the light source to the cornea, the one or more ultrasonic transducers being mounted on the structure.

The system recited above, wherein the control circuit is operative to determine deformation of the cornea from a rest position by determining a position of the cornea relative to a reference location based on the signals.

The system recited above, wherein the reference location is an element of the eye posterior to the cornea.

The system recited above, wherein the control circuit is operable to:

(a) determine a baseline value of the parameter before irradiation of the eye by the light source and one or more additional values of the parameter are commencement of irradiation by the light source, and compare each additional value to the baseline value to determine a change in the parameter; and (b) terminate the irradiation in response to a comparison between an additional response and the baseline response indicating a change in the response in excess of a predetermine threshold.

The system recited above, wherein the threshold is a function of the baseline response.

A method of corneal crosslinking comprising:

(a) irradiating a cornea in an eye of a living subject with light to induce crosslinking of collagen in the cornea; and (b) determining a resonant frequency of the cornea by (i) applying excitation ultrasonic energy amplitude modulated at a modulation frequency to the cornea;

(ii) varying the modulation frequency; and (iii) monitoring responses of the cornea induced by the excitation ultrasonic energy at different modulation frequencies and comparing the responses with one another to determine a modulation frequency which most closely corresponds to a resonant frequency of the cornea; and (c) controlling the irradiating step based at least in part on the modulation frequency determined in step (b).

A method as recited above wherein the step of applying excitation ultrasonic energy includes directing discrete pulses of the amplitude modulated excitation ultrasonic energy to the cornea with intervals between pulses, the step of varying the modulation frequency being performed so that the energy in different ones of the pulses is amplitude modulated at different frequencies.

A method as recited above wherein the step of monitoring responses of the cornea includes applying monitoring ultrasonic energy to the cornea and detecting the monitored ultrasonic energy reflected from the cornea during the intervals between pulses of excitation ultrasonic energy.

A system for corneal crosslinking comprising:

(a) a light source adapted to irradiate a cornea of an eye of a subject;

(b) means for applying a force to the cornea varying at a modulation frequency;

(c) means for monitoring a response of the cornea to the force;

(d) a control circuit connected to the force-applying means, the monitoring means and the light source, the control circuit being operable to vary the modulation frequency, compare the response of the cornea induced by forces at different modulation frequencies, determine a modulation frequency which most closely corresponds to a resonant frequency of the cornea, and control operation of the light source based at least in part on the modulation frequency.

A system as recited above wherein the means for applying a force includes a device adapted to rest on the eye of the subject, one or more ultrasonic transducers mounted on the device and a drive circuit operable to drive the one or more transducers with a carrier signal at an ultrasonic frequency and amplitude modulate the carrier signal at the modulation frequency.

A system as recited above wherein the means for applying a force includes an a parametric array of ultrasonic transducers operable to direct ultrasonic waves at a plurality of ultrasonic frequencies through the ambient air towards the eye of the subject so that the ultrasonic waves combine with one another at or near the eye to yield acoustic waves at the modulation frequency.

A method of controlling corneal crosslinking comprising the steps of:

(a) providing a finite-element model of the patient's eye in a pre-treatment condition;

(b) using the finite-element model, determining a desired post-treatment physical property of the cornea of the patient's eye which will bring the cornea to a desired shape;

(c) using the finite-element model, determining a predicted value of a measurable response of the cornea to a stimulus for the cornea having the desired post-treatment physical property;

(d) treating the cornea to bring about crosslinking by applying radiant energy to the cornea in the presence of a crosslinking agent; and (e) after commencement of the treating step, applying the stimulus to the cornea and measuring a response of the cornea to the stimulus; and (f) terminating the treating step when the measured response during the treating step reaches the predicted value.

A method as recited above wherein the step of developing the finite-element model includes measuring a response of the patient's eye to the stimulus before the treating step and selecting a pre-treatment physical property of the cornea used in the finite-element model so that a predicted response of the model matches the response measured before the treatment step.

A method as recited above wherein the step of applying the stimulus includes applying a force to the cornea.

A method as recited above wherein the step of applying a force to the cornea includes directing one or more push pulses of excitation ultrasonic energy to the cornea.

A system for corneal crosslinking comprising:

(a) a light source adapted to irradiate a cornea of an eye of a subject;

(b) means for applying a force to the cornea;

(c) means for measuring a response of the cornea to the force;

(d) a control circuit connected to the force-applying means, the monitoring means and the light source, the control circuit having stored therein a value representing a predicted post-treatment response of the cornea to the force the cornea having post-treatment material properties, the control circuit being operative to repeatedly actuate the force-applying means to apply the force to the cornea and receive measured responses from the measuring means after commencement of operation of the light source, compare the measured responses to the stored valued and terminate operation of the light source when the comparison indicates that a measured response corresponds to the stored value.

The foregoing description of certain embodiments of the invention should be taken by way of illustration, rather than limitation, of the present invention.

The invention claimed is:

1. A system for corneal crosslinking comprising:

(a) a light source adapted to irradiate a cornea of an eye of a subject;

(b) one or more ultrasonic transducers;

(c) a drive circuit connected to the one or more transducers, the drive circuit being operable to:

(i) actuate the transducers to repeatedly apply pulses of monitoring ultrasonic energy to the cornea; and (ii) derive signals representing ultrasonic energy returned from the cornea; and (d) a control circuit connected to the drive circuit and the light source, the control circuit being operable to repeatedly determine a position of a structure of the cornea relative to a reference location by determining a time of flight of the monitoring ultrasonic between the reference location and the structure of the cornea based on the signals so as to provide a baseline position before operation of the light source to irradiate the cornea and one or more additional positions during the operation of light source, wherein the reference location is selected from the group consisting of (i) an element of a device resting on the eye of the subject and (ii) an element of the eye of the subject posterior to the cornea, and wherein the control circuit is operable to compare the additional positions to the baseline position, and control operation of the light source based at least in part on the results of the comparison.

2. A system as claimed in claim 1 further comprising a device adapted to rest on the eye of the subject and to transmit light from the source to the cornea of the eye, the one or more transducers being mounted to the device.

3. A system as claimed in claim 2 wherein the reference location is a location of an element of the device.

4. A system as claimed in claim 1 wherein the reference location is an element of the eye posterior to the cornea.

5. A system as claimed in claim 4 wherein the reference location is a surface of the lens of the eye of the subject.

6. A system for corneal crosslinking comprising:

(a) a device adapted to rest an eye of a living subject;

(b) one or more ultrasonic transducers mounted to the device;

(c) a drive circuit connected to the one or more transducers, the drive circuit being operable to:

(i) actuate the transducers to repeatedly apply pulses of monitoring ultrasonic energy to the eye; and (ii) derive signals representing ultrasonic energy returned from the eye; and (d) a control circuit connected to the drive circuit and operable to:

(i) determine an anterior distance by measuring an anterior time of flight for ultrasound between an element of the device and an anterior surface of a corneal structure; and (ii) determine a posterior distance by measuring a posterior time of flight for ultrasound between an element of the eye posterior to the corneal structure and a posterior surface of the corneal structure; and (iii) subtracting the anterior and posterior distances from a reference distance between the element of the device and the element of the eye to yield the thickness of the corneal structure.

7. A system as claimed in claim 6 further comprising a light source connected to the control circuit, the device being operable to transmit light from the source to the cornea of eye, the control circuit being operable to determine the anterior and posterior distances at a measurement time after commencement of operation of the light source and to determine a thickness the corneal structure at the measurement time and to control operation of the light source at the measurement time.

8. A system as claimed in claim 7 wherein the control circuit is operable to determine the reference distance prior to operation of the light source by determining the anterior and posterior distance prior to operation of the light source, determine a thickness of the corneal structure by measuring a time of flight for ultrasound between the anterior and posterior surfaces of the corneal structure prior operation of the light source, and add the anterior distance, posterior difference and thickness to yield the reference difference.

9. A system as claimed in claim 7 wherein the control circuit is operable to determine a speed of sound in the corneal structure at the measurement time by determining a time of flight of ultrasound through the corneal structure at the measurement time and dividing the thickness of the corneal structure at the measurement time by the time of flight of ultrasound through the structure of the cornea at the measurement time.

10. A system as claimed in claim 9 wherein the control circuit is operable to control operation of the light source based at least in part on the speed of sound in the structure of the cornea at the measurement time.

11. A system for corneal crosslinking comprising:
(a) a light source adapted to irradiate a cornea of an eye of a subject;
(b) one or more ultrasonic transducers;
(c) a drive circuit connected to the one or more transducers, the drive circuit being operable to:
   (i) actuate the transducers to repeatedly apply pulses of monitoring ultrasonic energy to the cornea; and
   (ii) derive signals representing ultrasonic energy returned from the cornea; and
(d) a control circuit connected to the drive circuit and the light source, the control circuit being operable to determine from the signals a location of a surface of demarcation formed within stroma of the cornea formed by crosslinking responsive to irradiation by the light source and to control the operation of the light source based at least in part on the determined location of the surface of demarcation.

12. A system as claimed in claim 11 wherein the control circuit is operable to determine the location of the surface of demarcation by determining a distance between a naturally-occurring surface of the cornea and the surface of demarcation.

13. A system as claimed in claim 11 wherein the control circuit is operative to terminate operation of the light source when the location of the surface of demarcation reaches a predetermined threshold location.

* * * * *